United States Patent
Mathers

(10) Patent No.: US 7,189,189 B1
(45) Date of Patent: Mar. 13, 2007

(54) COMFORT TIME RELAXATION DEVICE

(76) Inventor: Diana Mathers, 1316 Camino del Sol, San Marcos, CA (US) 91069

( * ) Notice: Subject to any disclaimer, the term of this patent is extended or adjusted under 35 U.S.C. 154(b) by 0 days.

(21) Appl. No.: 11/211,851

(22) Filed: Aug. 24, 2005

(51) Int. Cl.
*A61B 5/00* (2006.01)
*A63B 22/00* (2006.01)

(52) U.S. Cl. .................. 482/1; 600/26; 600/27

(58) Field of Classification Search ........... 482/1–9, 482/900–902; 600/26–28
See application file for complete search history.

(56) References Cited

U.S. PATENT DOCUMENTS 5,647,834 A * 7/1997 Ron ..................... 600/23
6,554,763 B1 * 4/2003 Amano et al. ............. 600/26
6,702,767 B1 * 3/2004 Douglas et al. ............ 601/15

* cited by examiner

*Primary Examiner*—Glenn E. Richman
(74) *Attorney, Agent, or Firm*—Thomas I. Rozsa

(57) ABSTRACT

The present invention is a stress management device which relates to the field of health and is a portable device with auditory messages. The device can be carried by a user and used privately with ear phones or can be auditory and used with speakers. The present invention relaxation device can be used as needed when tension arises, or on a regular basis as a way to prevent tension buildup that can contribute to health problems. The battery operated device is activated by the user and has sequential recorded messages that remind the user at his or her pace to relax and release physical and mental tension.

17 Claims, 5 Drawing Sheets

COMFORT TIME RELAXATION DEVICE

BACKGROUND OF THE INVENTION

1. Field of the Invention

The present invention relates to the field of stress relief and stress management and in particular to devices which enable a user to relax and relieve the particular stress which the user is experiencing at any given moment.

2. Description of the Prior Art

Stress is a major cause of medical problems and can lead to serious medical conditions such as a stroke, heart attack, depression, etc. It is known by medical practitioners that stress is a major health issue and that approximately eighty percent (80%) of medical treatment visits are related to stress conditions. While psychologists and psychiatrists have attempted to treat stress with psychological counseling and medicines, these solutions are not readily available instantaneously to help an individual during a period of stress or anxiety. There is a significant need for a new and improved apparatus to instantaneously help a person to relieve their stress at any given moment.

SUMMARY OF THE INVENTION

The present invention is a stress management device which relates to the field of health and is a portable device with auditory messages. The device can be carried by a user and used privately with ear phones or can be auditory and used with speakers. The present invention relaxation device can be used as needed when tension arises, or on a regular basis as a way to prevent tension buildup that can contribute to health problems. The battery operated device is activated by the user and has sequential recorded messages that remind the user at his or her pace to relax and release physical and mental tension.

It has been discovered, according to the present invention, that if a stress relief apparatus which delivers relaxation messages in a desired sequence can be incorporated into a portable device which is activated by the user at any time, then a user can obtain instantaneous stress relief at any time and at any place through activation of the relaxation device.

It has further been discovered, according to the present invention, that a preselected series of relaxation messages delivered over and over can activate several parts of the brain to allow more awareness of the tension so it an be consciously released.

It has additionally been discovered, according to the present invention, that a portable device which delivers relaxation messages which causes the user to loosen the user's shoulders releases tension in the shoulder area where a large amount of tension usually builds up.

It has also been discovered, according to the present invention, that a portable device which delivers relaxation messages which causes the user to smile can release endorphins in the brain that can improve mood and increase energy.

It is therefore an object of the present invention to provide a portable stress relief apparatus which delivers relaxation messages in a desired sequence and which is activated by the user at any time, so that a user can obtain instantaneous stress relief at any time and at any place through activation of the relaxation device.

It a further object of the present invention to provide a preselected series of relaxation messages delivered over and over to thereby activate several parts of the brain to allow more awareness of the tension so it an be consciously released.

It is an additional object of the present invention to provide a portable device which delivers relaxation messages which causes the user to loosen the user's shoulders to thereby release tension in the shoulder area where a large amount of tension usually builds up.

It is also an object of the present invention to provide a portable device which delivers relaxation messages which causes the user to smile so that endorphins in the brain will be released to thereby improve mood and increase energy.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
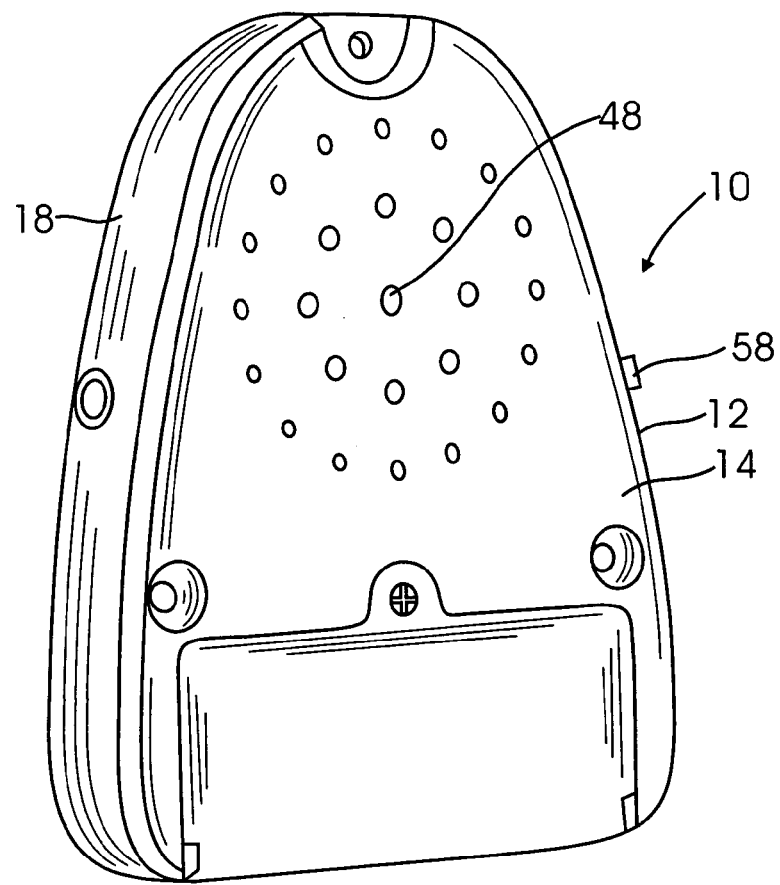
FIG. 1 is a perspective view of the front of the present invention relaxation device showing the speaker openings, the battery compartment, the earphone jack and the on-off switch.
Figures 2, 3:
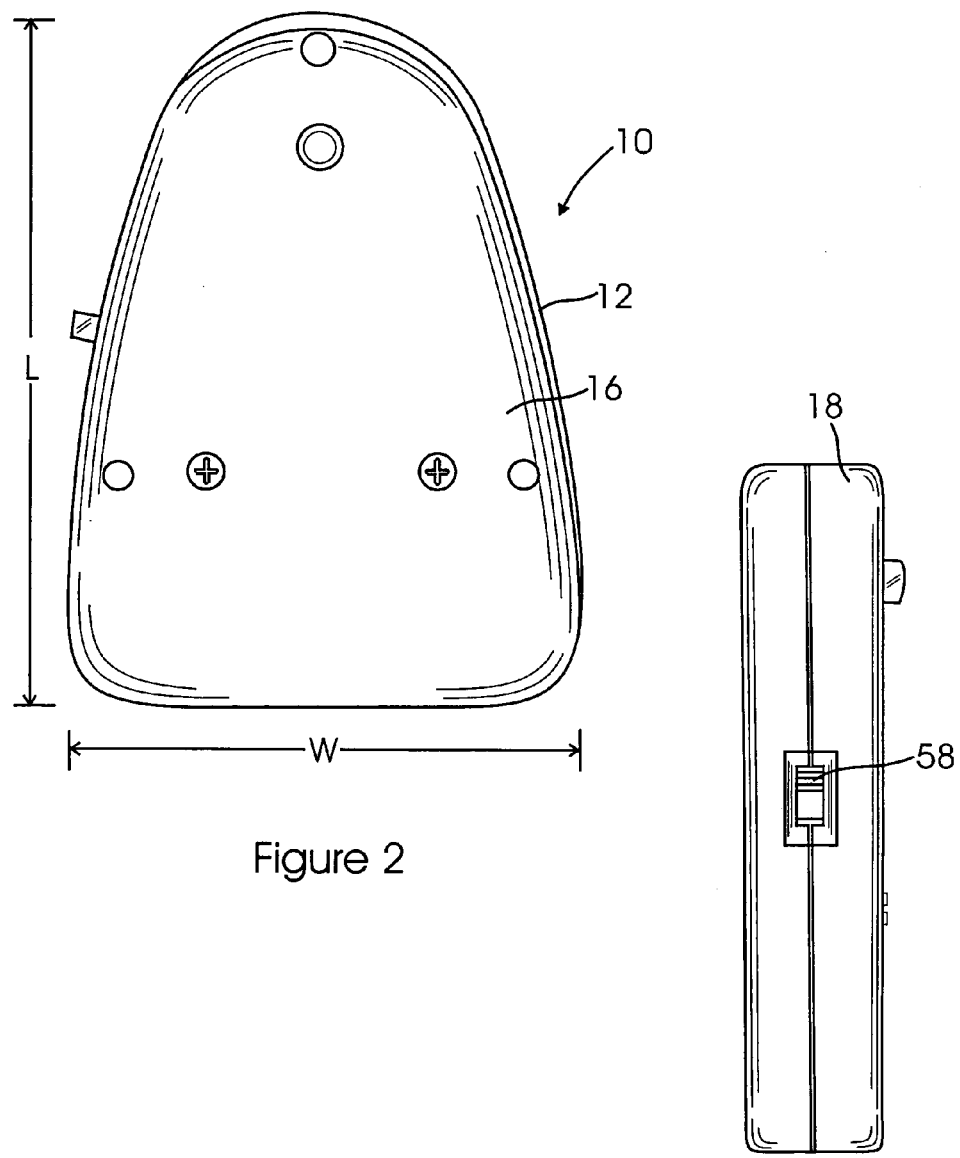
FIG. 2 is a rear elevational view of the present invention relaxation device.
FIG. 3 is a side elevational view from the right side of the interior of the present invention relaxation device.

Referring to FIGS. 1 and 2, there is illustrated one embodiment of the present invention relaxation device 10. The relaxation device 10 is enclosed in an exterior casing 12 having a front surface 14, a rear surface 16 and a circumferential sidewall 18 all of which serve to enclose an interior chamber 20. By way of example only, the casing can have a width "W" of approximately 2¾ inches and a length "L" of approximately 3¾ inches so that it can be easily fit in a person's shirt pocket, carried in a person's hand, or placed in a woman's purse.

Figure 4:
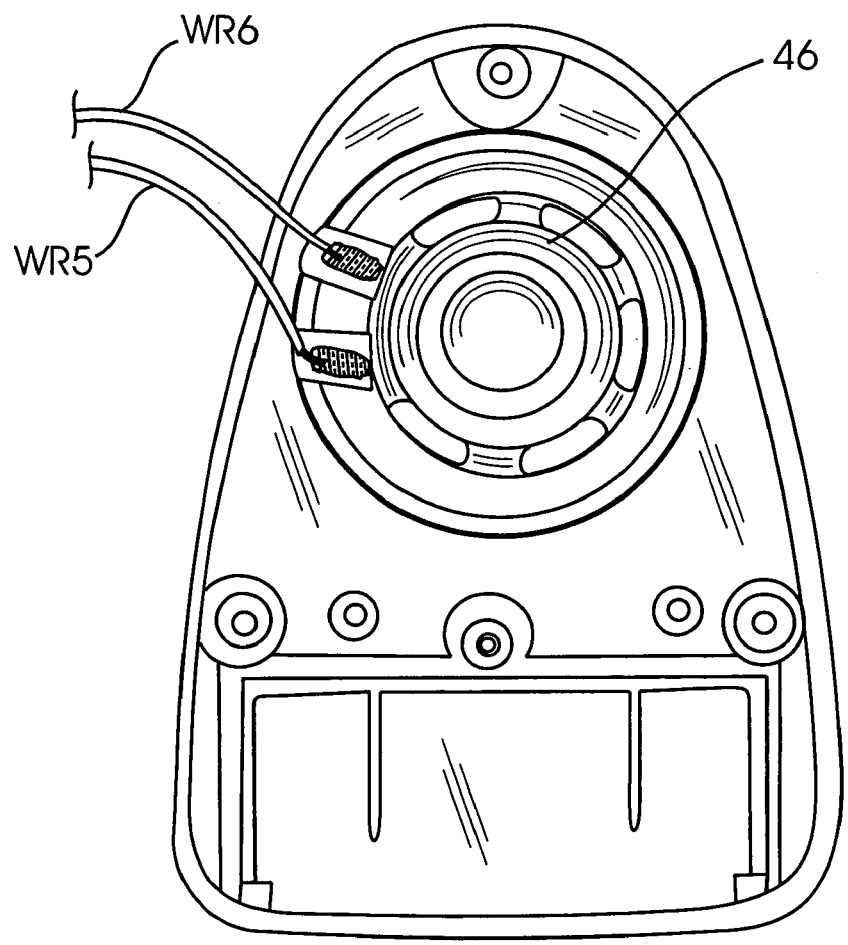
FIG. 4 is an open elevational view of the interio compartment from the front of the present invention relaxation device.
Figure 5:
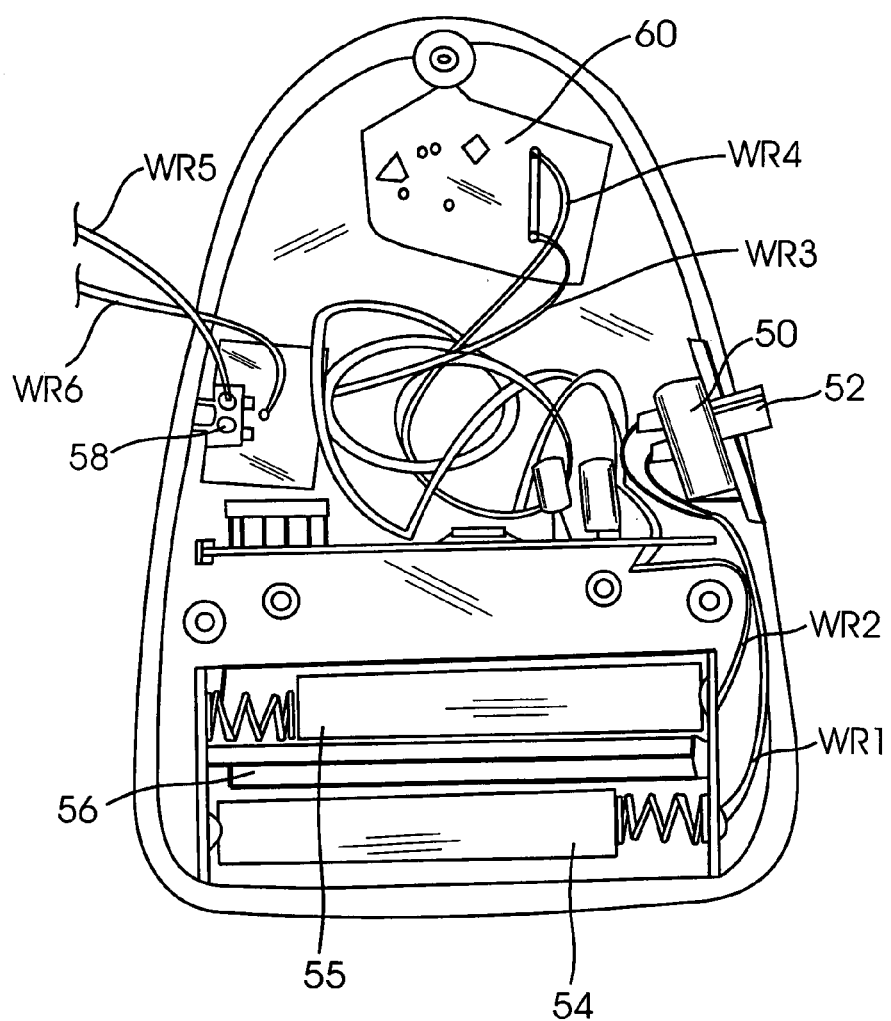
FIG. 5 is an open elevational view of the interior compartment from the rear of the present invention relaxation device.
Figure 6:
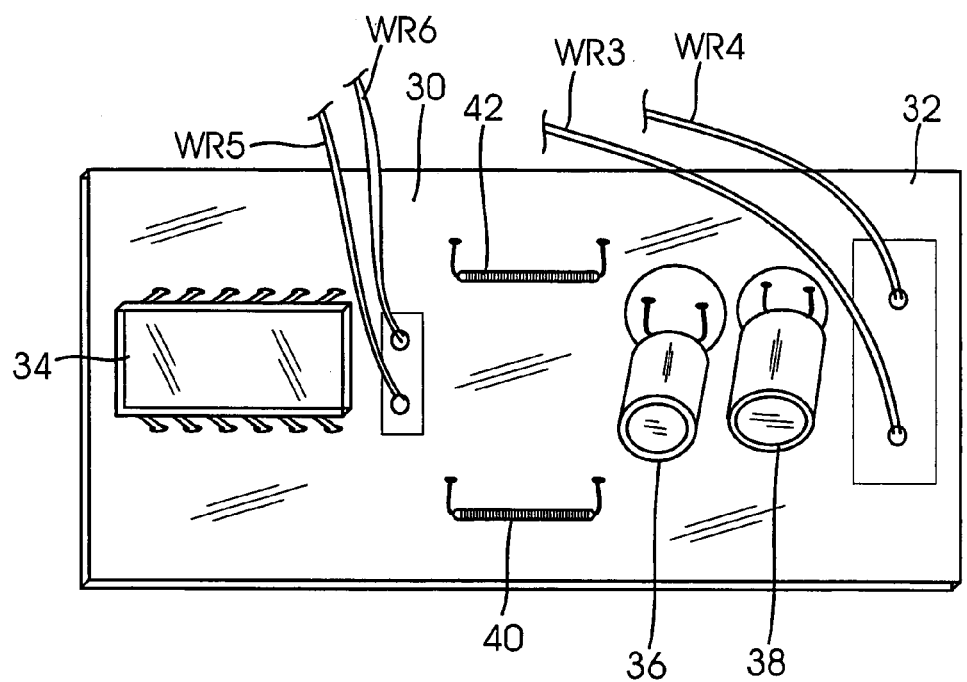
FIG. 6 is a perspective view of the electronic components of the present invention relaxation device.

Within interior chamber 20 is housed a circuit board 30, a schematic diagram of which is illustrated in FIG. 4. The circuit board 30 is single sided 32 which can be 0.040 inch thick, 1.9 inches long and 0.55 inches wide, using through hole technology. The circuit consists of one 8 pin dip part 34, a radial lead electrolytic capacitor 36, a TO-92 package device 38, and a three ⅛ watt axial lead resistors 40, 42 and 44. Also housed within chamber 20 is an audio transducer having one 1.5 inch diameter 16 ohm speaker 46 which has its auditory sound transmitted through speaker openings 48 in front wall 14 of housing 12. An earphone jack 50 is also connected to the speaker 46 so that a person can privately listen to the auditory messages. The circuit is powered by two AAA batteries 52 housed in a battery compartment 54. The relaxation device 10 has a pushbutton activation switch 56 which can be built into the rear surface 16 as illustrated in FIG. 2 or can be the alternative 56A wired pushbutton activation switch.

Contained within the TO-92 package 38 is a chip which can contain a series of selected pre-recorded messages thereon. The chip includes a series of sequential recorded messages that remind the user at his or her own pace to relax and release physical and mental tension. By way of example, the prerecorded messages can be: (1) Now it's comfort time for you; (2) Take a deep breath up from your feet, breath in slowly 1, 2, 3,4-breath out slowly 5, 6, 7, 8; (3) Now relax your shoulders, let them drop; and (4) Now smile. Feel the release through your body. The messages can be set to automatically play one after the other or alternatively, each message can stop after it has been delivered and it is necessary for the user to press the activation switch in order for the next message to be played.

The actions that the messages describe activate several parts of the brain. The relaxing process allows more awareness of tension so it can be consciously released.

Deep breathing provides additional oxygen which is relaxing. Loosening the shoulders, where many people carry a large amount of tension can soothe the whole body and allows more physical awareness.

Smiling can release endorphins in the brain that can improve mood and increase energy.

Through use of the present invention, the person can have instantaneous access to stress relief at any time and at any location. The small portable battery operated compact devices enables it to be conveniently carried by a person so that a person can use it at any place and time, such as at home, during work, when on vacation, when on a business trip, before making a public appearance, before a sporting event, before meeting with teachers at school, etc. Through the novel stress release system of the present invention, the user can obtain instantaneous stress release at any time and for as long as the user desires.

Defined in detail, the present invention is a relaxation device comprising: (a) an exterior casing having a front surface, a rear surface and an exterior sidewall all of which define the boundaries of an interior chamber, the front surface of the exterior casing having a multiplicity of speaker openings and an opening to gain access to a battery compartment housed within the chamber and containing batteries therein; (b) a circuit board having through hole technology housed within the chamber, the circuit board having an 8 pin dip part, a radial electrolytic capacitor, a TO-92 package device containing a memory chip having prerecorded messages therein, and three 1.8 watt axial resistors, at least one of the components of the circuit board connected to a speaker which can transmit auditory sound through the speaker openings, a pushbutton activation switch connected to at least one component of the circuit board, an earphone jack connected so as to cause the auditory sound to be transmitted through an earphone connected to the earphone jack, and at least one component of the circuit board connected to the batteries; (c) the memory chip containing sequential prerecorded messages which are (1) now it's comfort time for you, (2) take a deep breath up from your feet, breath in slowly 1, 2, 3,4-breath out slowly 5, 6, 7, 8, (3) now relax your shoulders, let them drop, and (4) now smile, feel the release through your body; and (d) the messages being initiated by pressing the pushbutton activation switch.

Defined broadly, the present invention is a relaxation device comprising: (a) an exterior casing having a front surface, a rear surface and an exterior sidewall all of which define the boundaries of an interior chamber, the front surface of the exterior casing having a multiplicity of speaker openings and an opening to gain access to a battery compartment housed within the chamber and containing batteries therein; (b) a circuit board housed within the chamber and containing a memory chip having prerecorded messages therein and components on the circuit board to enable the memory chip to be activated, at least one of the components of the circuit board connected to a speaker which can transmit auditory sound through the speaker openings, a pushbutton activation switch connected to at least one component of the circuit board, an earphone jack connected so as to cause the auditory sound to be transmitted through an earphone connected to the earphone jack, and at least one component of the circuit board connected to the batteries; (c) the memory chip containing sequential prerecorded messages which are (1) now it's comfort time for you, (2) take a deep breath up from your feet, breath in slowly 1, 2, 3,4-breath out slowly 5, 6, 7, 8, (3) now relax your shoulders, let them drop, and (4) now smile, feel the release through your body; and (d) the messages being initiated by pressing the pushbutton activation switch.

Defined even more broadly, the present invention is a relaxation device comprising: (a) an exterior casing having exterior walls which define an interior chamber, at least one wall of the casing having means to permit auditory sound to be transmitted through the casing and power supply means housed within the casing; (b) a circuit board housed within the chamber and containing a memory chip having prerecorded messages therein and components on the circuit board to enable the memory chip to be activated, at least one of the components of the circuit board connected to a speaker which can transmit auditory sound through the means on the casing wall, activation means connected to at least one component of the circuit board, and means to connect at least one component of the circuit board to the power supply means; (c) the memory chip containing sequential prerecorded messages which are at least one message selected from the group comprising: (1) now it's comfort time for you, (2) take a deep breath up from your feet, breath in slowly 1, 2, 3,4-breath out slowly 5, 6, 7, 8, (3) now relax your shoulders, let them drop, and (4) now smile, feel the release through your body; and (d) the messages being initiated through the activation means.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A relaxation device comprising:
   a. an exterior casing having a front surface, a rear surface and an exterior sidewall all of which define the boundaries of an interior chamber, the front surface of the exterior casing having a multiplicity of speaker openings and an opening to gain access to a battery compartment housed within the chamber and containing batteries therein;
   b. a circuit board having through hole technology housed within said chamber, said circuit board having an 8 pin dip part, a radial electrolytic capacitor, a TO-92 package device containing a memory chip having prerecorded messages therein, and three 1.8 watt axial resistors, at least one of the components of the circuit board connected to a speaker which can transmit auditory sound through said speaker openings, a pushbutton activation switch connected to at least one component of said circuit board, an earphone jack connected so as to cause the auditory sound to be transmitted through an earphone connected to the earphone jack, and at least one component of the circuit board connected to the batteries;
   c. said memory chip containing sequential prerecorded messages which are (1) now it's comfort time for you, (2) take a deep breath up from your feet, breath in slowly 1, 2, 3,4-breath out slowly 5, 6, 7, 8, (3) now relax your shoulders, let them drop, and (4) now smile, feel the release through your body; and
   d. said messages being initiated by pressing said pushbutton activation switch.

2. The relaxation device in accordance with claim 1 wherein said prerecorded messages are played through said speaker and emanate through said speaker holes.

3. The relaxation device in accordance with claim 1 wherein said prerecorded messages are played through an earphone connected to said earphone jack.

4. The relaxation device in accordance with claim 1 wherein said prerecorded messages are played sequentially one after another after the pushbutton switch is activated.

5. The relaxation device in accordance with claim 1 wherein said prerecorded messages are played one at a time with each subsequent message only played after the pushbutton activation switch is activated.

6. A relaxation device comprising:
   a. an exterior casing having a front surface, a rear surface and an exterior sidewall all of which define the boundaries of an interior chamber, the front surface of the exterior casing having a multiplicity of speaker openings and an opening to gain access to a battery compartment housed within the chamber and containing batteries therein;
   b. a circuit board housed within said chamber and containing a memory chip having prerecorded messages therein and components on said circuit board to enable the memory chip to be activated, at least one of the components of the circuit board connected to a speaker which can transmit auditory sound through said speaker openings, a pushbutton activation switch connected to at least one component of said circuit board, an earphone jack connected so as to cause the auditory sound to be transmitted through an earphone connected to the earphone jack, and at least one component of the circuit board connected to the batteries;
   c. said memory chip containing sequential prerecorded messages which are (1) now it's comfort time for you, (2) take a deep breath up from your feet, breath in slowly 1, 2, 3,4-breath out slowly 5, 6, 7, 8, (3) now relax your shoulders, let them drop, and (4) now smile, feel the release through your body; and
   d. said messages being initiated by pressing said pushbutton activation switch.

7. The relaxation device in accordance with claim 6 wherein said prerecorded messages are played through said speaker and emanate through said speaker holes.

8. The relaxation device in accordance with claim 6 wherein said prerecorded messages are played through an earphone connected to said earphone jack.

9. The relaxation device in accordance with claim 6 wherein said prerecorded messages are played sequentially one after another after the pushbutton switch is activated.

10. The relaxation device in accordance with claim 6 wherein said prerecorded messages are played one at a time with each subsequent message only played after the pushbutton activation switch is activated.

11. A relaxation device comprising:
    a. an exterior casing having exterior walls which define an interior chamber, at least one wall of the casing having means to permit auditory sound to be transmitted through the casing and power supply means housed within said casing;
    b. a circuit board housed within said chamber and containing a memory chip having prerecorded messages therein and components on said circuit board to enable the memory chip to be activated, at least one of the components of the circuit board connected to a speaker which can transmit auditory sound through said means on said casing wall, activation means connected to at least one component of said circuit board, and means to connect at least one component of the circuit board to said power supply means;
    c. said memory chip containing sequential prerecorded messages which are at least one message selected from the group comprising: (1) now it's comfort time for you, (2) take a deep breath up from your feet, breath in slowly 1, 2, 3,4-breath out slowly 5, 6, 7, 8, (3) now relax your shoulders, let them drop, and (4) now smile, feel the release through your body; and
    d. said messages being initiated through said activation means.

12. The relaxation device in accordance with claim 11 further comprising an earphone jack connected so as to cause the auditory sound to be transmitted through an earphone connected to the earphone jack.

13. The relaxation device in accordance with claim 11 where said power supply means is at least one battery.

14. The relaxation device in accordance with claim 11 wherein said prerecorded messages are played through said speaker and emanate through said speaker holes.

15. The relaxation device in accordance with claim 11 wherein said prerecorded messages are played through an earphone connected to said earphone jack.

16. The relaxation device in accordance with claim 11 wherein said prerecorded messages are played sequentially one after another after the pushbutton switch is activated.

17. The relaxation device in accordance with claim 11 wherein said prerecorded messages are played one at a time with each subsequent message only played after the pushbutton activation switch is activated.

* * * * *